(12) United States Patent
Bauer et al.

(10) Patent No.: US 11,605,866 B2
(45) Date of Patent: Mar. 14, 2023

(54) COMPACT INTEGRATED ROTARY JOINT

(71) Applicant: Schleifring GmbH, Fürstenfeldbruck (DE)

(72) Inventors: Lukas Bauer, Fürstenfeldbruck (DE); Ulrich Herrmann, Munich (DE); Holger Häffner, Schwabmünchen (DE); Markus Wilhelm, Kaufering (DE)

(73) Assignee: SCHLEIFRING GmbH, Fürstenfeldbruck (DE)

( * ) Notice: Subject to any disclaimer, the term of this patent is extended or adjusted under 35 U.S.C. 154(b) by 0 days.

(21) Appl. No.: 17/743,209

(22) Filed: May 12, 2022

(65) Prior Publication Data

US 2022/0344884 A1  Oct. 27, 2022

Related U.S. Application Data

(63) Continuation of application No. PCT/EP2020/082104, filed on Nov. 13, 2020.

(30) Foreign Application Priority Data

Nov. 14, 2019 (EP) .................................. 19209173

(51) Int. Cl.
*H01F 38/18* (2006.01)
*H01P 1/06* (2006.01)
(Continued)

(52) U.S. Cl.
CPC ............. *H01P 1/062* (2013.01); *H01F 38/18* (2013.01); *H01R 39/08* (2013.01); *H05K 1/0237* (2013.01); *H05K 1/0298* (2013.01)

(58) Field of Classification Search
CPC ......... H01P 1/062; H01F 38/18; H01R 39/08; H05K 1/0237; H05K 1/0298
(Continued)

(56) References Cited

U.S. PATENT DOCUMENTS 5,530,424 A   6/1996  Harrison et al.
7,717,619 B2  5/2010  Katcha et al.
(Continued)

FOREIGN PATENT DOCUMENTS

CN   207926288 U    9/2018
DE   102015121432 A1  6/2017
(Continued)

OTHER PUBLICATIONS

Trevisan et al.. Wireless Sensing and Power Transfer in a Rotary Tool, IEEE MTT-S International Microwave Symposium, 2015, pp. 1-4.
(Continued)

*Primary Examiner* — Terrance L Kenerly

(74) *Attorney, Agent, or Firm* — Quarles & Brady LLP; Yakov S. Sidorin

(57) ABSTRACT

A rotary joint includes a first part and a second part configured to rotate around a rotation axis against the first part. The first part has a first magnetic core, a sliding brush, and a capacitive data link component. The second part has a second magnetic core for coupling power with the first magnetic core, a sliding track for galvanic coupling with the sliding brush, and a second capacitive data link component to transfer data from and/or to the first capacitive data link component. To weaken magnetic stray fields from the magnetic core, the rotary joint is a disc-type rotary joint, and the sliding track is arranged radially between the second magnetic core and the second capacitive data link component.

22 Claims, 6 Drawing Sheets

(51) Int. Cl.
  *H05K 1/02* (2006.01)
  *H01R 39/08* (2006.01)
(58) Field of Classification Search
  USPC .......................................................... 310/232
  See application file for complete search history.

(56) References Cited

U.S. PATENT DOCUMENTS

| | | |
|---|---|---|
| 9,136,912 B2 | 9/2015 | West et al. |
| 2002/0057164 A1 | 5/2002 | Jin et al. |
| 2016/0211701 A1 | 7/2016 | Krumme |
| 2016/0276871 A1 | 9/2016 | Schmitz et al. |
| 2018/0037421 A1 | 2/2018 | Tam et al. |

FOREIGN PATENT DOCUMENTS

| | | |
|---|---|---|
| EP | 2109866 B1 | 4/2015 |
| EP | 2933655 A1 | 10/2015 |
| EP | 2954844 A1 | 12/2015 |
| GB | 1321940 | 7/1973 |

OTHER PUBLICATIONS

Trevisan et al., A UHF Near-Field Link for Passive Sensing in Industrial Wireless Power Transfer Systems, IEEE Transactions on Microwave Theory and Techniques, 2016, 64(5):1634-1643.
European Patent Office, Extended Search Report, Application No. 20207516.4, dated Mar. 19, 2021, 9 pages.
PCT International Search Report and Written Opinion, PCT/EP2020/082104, dated Feb. 4, 2021, 15 pages.

COMPACT INTEGRATED ROTARY JOINT

CROSS-REFERENCE TO RELATED APPLICATIONS

This application is a continuation of pending International Application No. PCT/EP2020/082104 filed on Nov. 13, 2020 and now published as WO 2021/094564, which designates the United States and claims priority from the European Application No. 19209173.4 filed on Nov. 14, 2019. The disclosure of each of these patent documents is incorporated by reference herein.

FIELD OF THE INVENTION

The invention relates to slipring devices and rotary joints for transmission of multiple electrical signals between rotating parts.

DESCRIPTION OF RELATED ART

Electrical sliprings and rotary joints are used to transfer electrical power and/or signals between a rotating and a stationary part. Such sliprings are used in different applications, like wind energy plants or computer tomography scanners. There are also many industrial, military, and aerospace applications in which sliprings are used.

Electrical sliprings and rotary joints should be compact, reliable, and affordable.

U.S. Pat. No. 7,717,619 discloses a rotary joint including inductive power transfer and capacitive data transfer. The capacitive data links are distant from the inductive power couplers. As this is a comparatively large rotary joint for CT scanners, spacing between the links is no problem.

EP 2 933 655 A1 discloses a compact rotary joint with inductive power transfer and capacitive data transfer. Here, capacitive couplers are arranged partially within the magnetic cores to save space. This is acceptable, because only a low bandwidth for control signals is required.

EP 2 954 844 A1 discloses a rotary joint with an inductive power coupler and slipring tracks in an axial arrangement (disc-type) and capacitive datalinks in a radial arrangement (drum-type). This consumes much space but allows to arrange the datalinks such, that there is only a minimal effect from the magnetic field of the inductive power coupler. The datalinks are parallel to the magnetic field lines and therefore do pick up any fields. Unfortunately, this consumes much space.

SUMMARY

The embodiments are providing a compact rotary joint providing at least inductive power transfer and capacitive data transfer with a high data rate.

In an embodiment, a slipring device includes a first part and a second part which are rotatable against each other about a center axis. For example, the first part may be stationary, whereas the second part may be rotating relative thereto. Of course, the rotating and stationary parts may be exchanged or even both parts may be rotating with different speeds.

The first part may have a first housing which may contain first rotary joint components like inductive coupling components, capacitive coupling components and slip rings. These may be arranged on a first printed circuit board (PCB) which may have a sliding track as a PCB trace, and/or a brush mounted and/or soldered to the PCB.

The second part may have a second housing which may contain second rotary joint components like inductive coupling components, capacitive coupling components and slip rings. These may be arranged on a second printed circuit board which may have a sliding track as a PCB trace, and/or a brush mounted and/or soldered to the PCB.

The rotary joint components in the first part and the second part are designed such that they interface in a way to form inductive, capacitive, or sliding contact connections. Therefore, a contact brush at the first part may interface with a sliding track at the second part and/or a contact brush at the second part may interface with a sliding track at the first part. An inductive coupler at the first part may interface with an inductive coupler at the second part and a capacitive coupler at the first part may interface with a capacitive coupler at the second part. There may be multiple connections between the first part and the second part.

For holding the first part and the second part in a spatial relationship and allowing rotation therebetween, preferably at least one bearing is provided. Such a bearing may be a slide bearing, a ball bearing, a liquid bearing, or any other suitable bearing. Preferably, a ball bearing and most preferably two ball bearings are provided.

An embodiment relates to a disk-shaped rotary joint, also called platter rotary joint. Here, the main components may be approximately arranged in or close to a common plane. Such a plane may be orthogonal to the rotation axis.

In this embodiment, a rotary joint includes an inductive coupling component, further including at least a first magnetic core on the first part and a second magnetic core on the second part. Within the first magnetic core is a first winding, and within the second magnetic core is a second winding. The first winding and the second winding are magnetically coupled with each other through the first magnetic core and the second magnetic core. While one of the windings may be connected to an AC signal generator, the other may be connected to a rectifier for delivering power to a circuit connected to the winding. The first magnetic core and the second magnetic core are held in a distance which forms an airgap between the cores.

Further, at least one galvanic slipring connection is provided by at least one sliding brush at the first part being in galvanic contact with at least one sliding track at the second part. To improve contact and reduce noise and resistance, multiple sliding brushes may be provided. The galvanic contact may be used for grounding of the circuit. There may be multiple slipring connections, further, brush and track may be exchanged.

The brush may also be located on the outer side of the PCB, e.g. placed as Surface mounted part, this way the brush may use the thickness of the PCB as spring travel distance further miniaturizing the design in an axial direction. A longer spring travel allows a lower variation of the spring force during the brush lifetime decreasing wear effects. The PCB in this case has a cutout for the spring in addition to pads for mounting the spring by soldering and optionally gluing.

The slipring track might be an outer layer of the printed circuit board with electrically and mechanically parallel tracks on inner layers sharing the current to reduce ohmic resistance of the track. The track might also be a separate circular metal sheet fixed into a circular groove of the printed circuit board.

In addition, at least one capacitive data link is provided. Such capacitive data link may include a first capacitive data link component on the first part in correspondence with a second capacitive data link component on the second part.

One of these capacitive data links may be a unidirectional component for transmitting data, whereas the other component may be a unidirectional component for receiving data. In an alternative embodiment, both components may be bidirectional components for transmitting and receiving data. If at one part, a unidirectional component for transmitting data is provided, corresponding thereto on the second part, a unidirectional component for receiving data is provided, and vice versa. There may be multiple capacitive data links.

The magnetic cores are arranged radially closer to the rotational axis, which is also the center axis of the rotary joint, than the galvanic slipring connection and the at least one capacitive data link, such that the galvanic slipring connection is positioned between the at least one capacitive data link and the magnetic cores. There may be a free bore around the center axis, such that other components like optical rotary joints or media rotary joints may be fed through the rotary joint. The magnetic core may have an inner diameter in the range of 1 cm to 2 m, depending on the requirement and the size of the rotary joint. In an embodiment, the magnetic core has an inner diameter between 5 cm and 10 cm and an outer diameter between 8 cm and 15 cm. The width of the magnetic core is determined by the size of the required magnetic material and may be in the range from 2 cm to 20 cm. The magnetic core may include ferrite material, iron material, or any other suitable soft-magnetic material. The capacitive data links are arranged outside of the magnetic cores and they may be arranged distant from the magnetic cores to avoid interference by the magnetic fields of the magnetic cores.

The galvanic slipring contact is arranged between the magnetic cores and the at least one capacitive data link. This increases the distance between the at least one capacitive data link and the magnetic cores without wasting space and thereby reduces interference.

Interference between the magnetic cores and the at least one capacitive data link is a critical design issue, as the capacitive data links have only a very weak coupling between the two parts, due to a very small coupling capacitance in the range of a few Picofarad (pF), and the magnetic cores handle comparatively high power levels. Signals coupling from the magnetic cores into the at least one capacitive data link may affect the signals coupled in the capacitive data link.

Specifically, in compact rotary joints, space and costs are critical design issues. Therefore, the magnetic cores are normally designed in such a way that the magnetic field strength and therefore the magnetic flux in the magnetic cores are dimensioned such that it is close to the maximum flux of the magnetic material. If a magnetic core is operated close to its maximum flux, it starts to produce magnetic flux outside of the core, thus generating a magnetic field protruding from the core to its environment and therefore also protruding into other components of the rotary joint. The effects of this stray field may be reduced by separating the components which would further increase the size of the rotary joint, which is not desired. Therefore, a shielding may be provided to reduce the interference of the magnetic field with the capacitive data links. Such a shield should be simple, inexpensive and should not consume much space. Therefore, providing a further housing around the magnetic core for providing additional shielding or at least reducing the stray field is not desired.

In this embodiment, placement of the galvanic contact system between the magnetic cores and the at least one capacitive data link will further reduce the stray field, because the field exiting the core and going through the environment of the core may cross the galvanic sliding contact system and specifically the galvanic sliding track. Such, at least one sliding track may have a distance to at least one first capacitive data link component or at least one second capacitive data link component which is larger than the distance between the at least one sliding track and at least one first magnetic core or at least one second magnetic core. To improve shielding, at least one sliding track may have a distance to at least one first magnetic core or at least one second magnetic core which is less than one of 10 times, 5 times, 3 times, 1 time the distance between the magnetic cores (i.e. the size of the airgap).

A galvanic sliding track normally is a closed ring of a low resistance conductive structure, in which the magnetic fields generate eddy currents, which leads to a weakening of the magnetic field. This further reduces interference with the at least one capacitive data link. To improve this effect, the sliding track may be increased in its size, preferably in its width, but also in its thickness, which would further lead to a higher current capacity of the sliding contact system. Accordingly, at least one sliding track may have a width wider than at least one of 2 mm, 8 mm, 10 mm, 15 mm and narrower than at least one of 50 mm, 40 mm, 30 mm, 20 mm, 10 mm, 5 mm. Alternatively, the at least one sliding track may be wider than the distance between the at least one first magnetic core and the at least one second magnetic core.

The galvanic contact system may be in a plane between the magnetic cores. The galvanic contact system may be close to an airgap between the magnetic cores. At least one sliding track may be arranged below a plane defined by the airgap between the magnetic cores and at least one sliding brush is mounted above the plane. This plane may be the same as the common plane mentioned above. It may also differ, if for example the magnetic cores have an axial offset to the capacitive data links.

BRIEF DESCRIPTION OF THE DRAWINGS

In the following, the invention will be described by way of example, without limitation of the general inventive concept, on examples of embodiment and with reference to the drawings.

Figure 1:
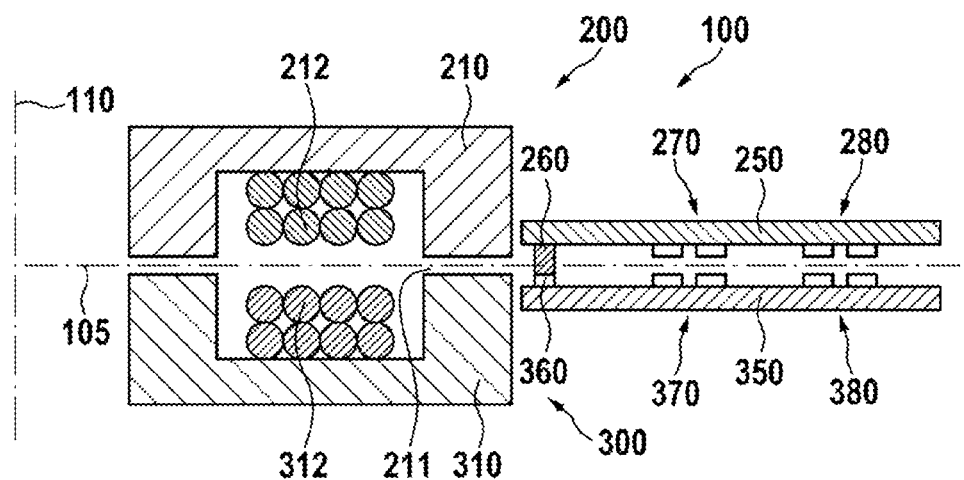
FIG. 1 shows a sectional view of a rotary joint.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

In FIG. 1, a sectional view of a disk-type rotary joint 100 is shown. The rotary joint has a center axis 110 which is the rotation axis of the rotary joint. Orthogonal to the center axis 110 is a plane of rotation 105. This may roughly be a plane of symmetry between a first part 200 and a second part 300 rotating against each other. In this Figure, the first part 200 of the rotary joint is above the plane of rotation 105, whereas the second part 300 of the rotary joint is below the plane of rotation 105. The first part 200 may include a first magnetic core 210, further including at least one first winding 212. The first winding 212 may include a plurality of wires or cables which may be insulated against each other and which may be wound in or around the magnetic core. In this embodiment, the magnetic core is a U-shaped core. The magnetic core may also be an E-shaped core or may have any other suitable shape. To provide a good coupling between the first part and the second part, the first magnetic core 210 and the second magnetic core 310 could form a closed magnetic circuit with minimal air gaps 211 between them. Such air gaps are hardly to avoid because the first part is rotatable against the second part. If the air gap is closed, there would be a high friction.

The first part of the rotary joint further includes at least one sliding brush 260, which may be a carbon brush or a metal brush, at least one first capacitive data link component 270, and it may further include an alternate first capacitive data link component 280. All these parts may be held and/or contained on a first printed circuit board (PCB) 250.

The second part 300 includes a second magnetic core 310 further including a second winding 312, which may be like the first winding 212. If a change in voltage between the input and output voltage of the rotating transformer is desired, there may be different numbers of windings in the first winding 212 and the second winding 312. Further, the second part includes a sliding track 360 and it may further include a second capacitive data link component 370 as well as an optional alternate second capacitive data link component 380. All these parts may be held by or integrated into a second printed circuit board (PCB) 350. As shown here, the galvanic slipring system including the sliding brush 260 and the sliding track 360 are arranged in radial direction with respect to the rotation axis 110 between the first 210 and second 310 magnetic cores and the first 270 and second 370 capacitive data link components. In a radial direction, the galvanic slipring components may be arranged outside of the magnetic cores and inside of the capacitive data link components. The sliding track 360 may be a low resistance track designed for high current capability. As it is placed close to the magnetic cores, stray fields from the magnetic cores will generate eddy currents in the sliding track and therefore these magnetic stray fields will be weakened. accordingly, the presence of the sliding track weakens the stray fields.

Figure 2:
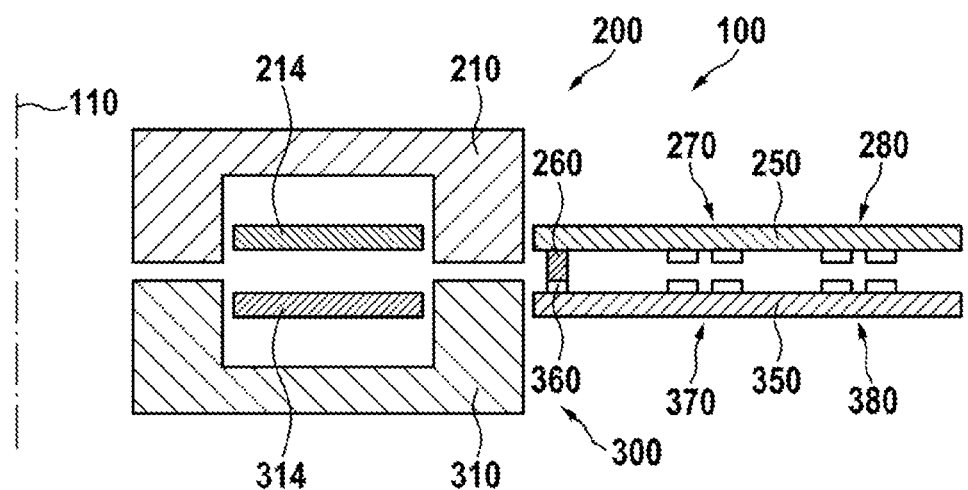
FIG. 2 shows a different embodiment.

In FIG. 2, a different embodiment is shown, where instead of wires of the first winding 212 and the second winding 312, printed circuit boards 214 and 314 are used. Making a coil structure on printed circuit boards is a much simpler and more inexpensive manufacturing process compared to manually winding wires into the magnetic cores. Such printed circuit board traces normally have a lower current capacity compared to solid copper wires, but they can be used in many applications, specifically were a comparatively low power is coupled. If a lower power is coupled, the magnetic cores may further be reduced in their size, which further leads to a reduction in total size of the rotary joint.

Figure 3:
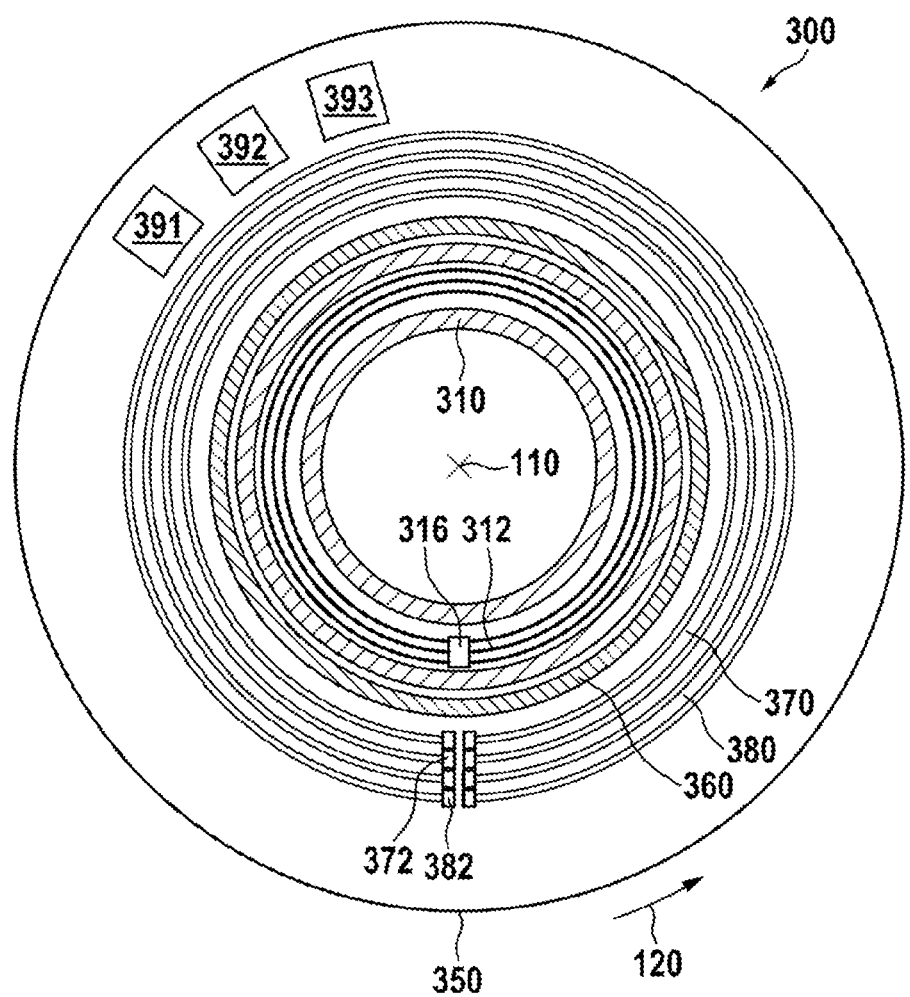
FIG. 3 shows a top view of an embodiment.

In FIG. 3, a top view of an embodiment of the second part 300 is shown. This Figure is further showing many features previously explained in FIGS. 1 and 2. In addition, a winding termination 316 for the second winding is shown. This winding termination may be an opening or a duct through which the winding is fed out of the magnetic core. The second magnetic core 310 is shown as one piece. In an embodiment, the first magnetic core 210 and/or the second magnetic core 310 may be made of multiple pieces or segments. Further, a second capacitive data link termination 372 is shown, which terminates the lines of the second capacitive data link component 370. An alternate second capacitive data link termination 382 may be provided to terminate the lines of the alternate second capacitive data link component 380. The arrow 120 indicates a possible direction of rotation, although the part 300 may rotate in an opposite direction or may rotate alternatingly. There may be further electrical and/or electronic components 391, 392 and 393 which may include at least one of a connector, an amplifier, a signal processing device and a microcontroller.

Figure 4:
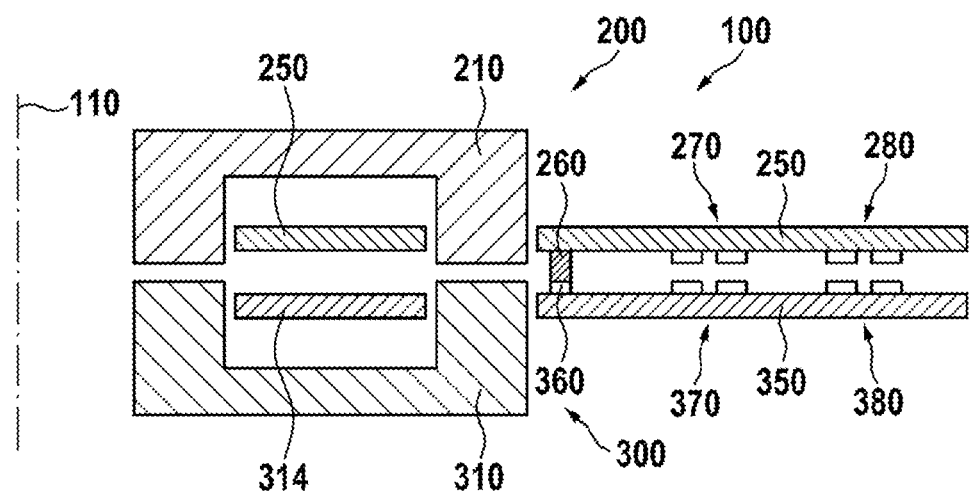
FIG. 4 shows an embodiment with a single PCB.

In FIG. 4, an embodiment with a single printed circuit board (PCB) 250 at the first part and a single PCB 350 at the second part is shown. Here, the first PCB 250 penetrates the magnetic core 210 to provide the windings therein. Also, the second PCB 350 penetrates the second magnetic core 310 to provide further windings therein. For the penetrations of the PCB into the cores, the cores may have at least one cutout.

Figure 5:
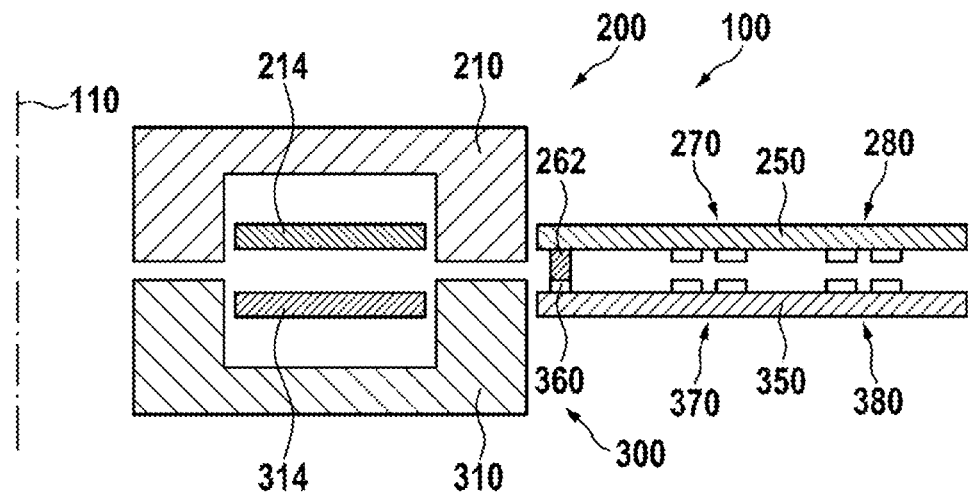
FIG. 5 shows an embodiment with a metal spring brush.

In FIG. 5, an embodiment with a metal spring brush is shown. Here, a flat metal spring brush 262 is provided for contacting the sliding track 360. Details of the brush are shown in the next figure.

Figure 6:
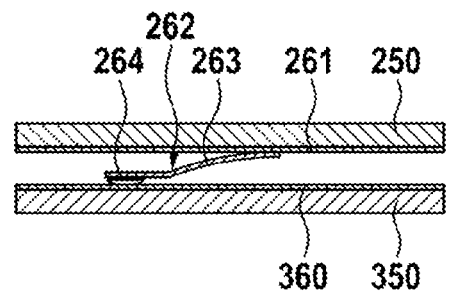
FIG. 6 shows details of a metal spring brush.

In FIG. 6, further details of a metal spring brush contact system are shown. At the bottom of this Figure is second PCB 350 with sliding track 360 on it. Opposing thereto is first PCB 250 with a flat metal spring brush 262 attached. It may be attached by soldering, welding, riveting, or a combination thereof or any other suitable attachment process which provides a good electric galvanic contact between the flat metal spring brush and at least one conductive trace on the printed circuit board 250. The flat metal spring brush 262 includes a metal spring 263 which may be made out of sheet metal or of a wire and which may include a contact element 264 at an end distant from the other end attached to the printed circuit board. This contact element 264 may be an extra plating at the flat metal spring brush, for example a gold or silver plating to increase conductivity and contact properties. It may also be an extra piece of metal or carbon or any other conductive material attached to the metal spring 263. There may be a circular conductive track 261 on the first PCB 250 for contacting the sliding brush 262. This track would provide further shielding and would provide a good electrical contact. Further, there may be multiple flat metal spring brushes 262 connected to said track and arranged on a circle around the center axis 110. This arrangement provides best shielding characteristics, if the distance (or gap) in an axial direction between the electrically conductive track 261 and the sliding track 360 is less or equal than an air gap 211 between the magnetic cores 210, 310. Multiple brushes may improve the contact performance, such as decreasing contact resistance and decreasing contact noise.

Figure 7:
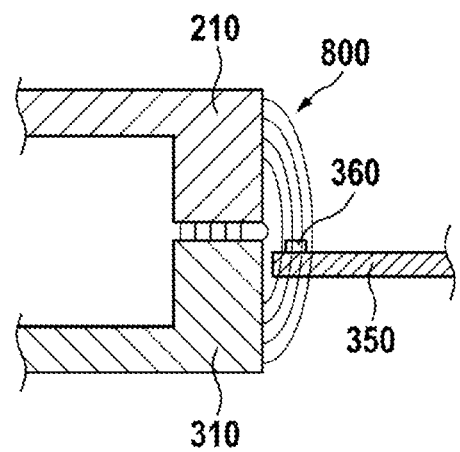
FIG. 7 shows magnetic fields of the magnetic cores in details.

In FIG. 7, details of the magnetic fields of the magnetic cores are shown. The Figure shows enlarged a first magnetic core 210 and a second magnetic core 310. There are always magnetic fields 800 outside of the magnetic cores. These are also called stray fields. At low flux within the magnetic core, these outside stray fields are comparatively weak. If the flux in the core is increased and is approaching saturation of the core, stray fields increase. This may lead to unacceptable high magnetic fields outside of the magnetic core, which may interfere with the capacitive data links. Therefore, a sliding track 360 is provided between the capacitive data links and the magnetic cores, such that the magnetic field in the sliding track generates eddy currents which lead to weakening of the magnetic fields. As mentioned before, opposing to the sliding track 360, there may be another electrically conductive track on first PCB 250 for contacting at least one sliding brush or multiple sliding brushes.

Figure 8:
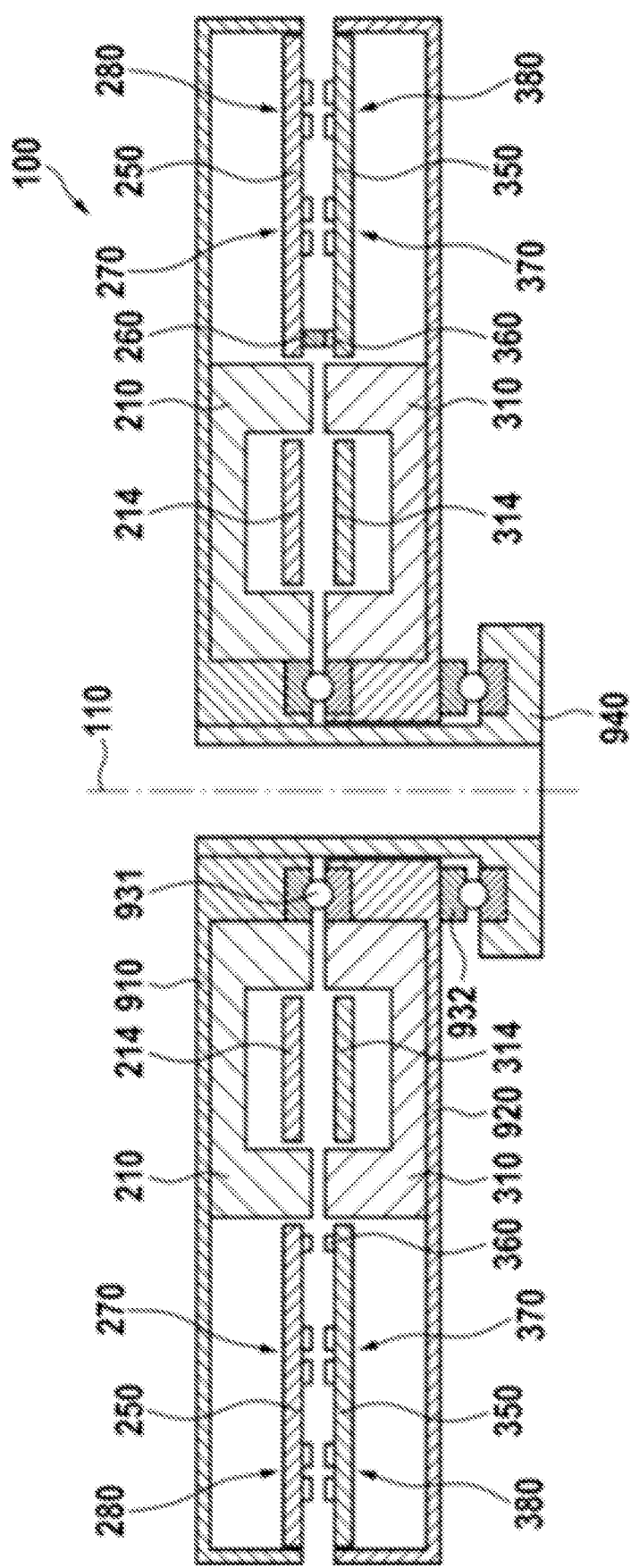
FIG. 8 shows an example of a housing with an integrated rotary joint.

In FIG. 8, an example of a housing with an integrated rotary joint is shown. Here, the components described before are integrated into a housing including a first housing section 910 and a second housing section 920. The first housing section 910 holds the first part 200, whereas the second housing section 920 holds the second part 300. There may be at least a first bearing 931 between the first housing section 910 and the second housing section 920 to hold these in a well-defined position relative to each other while allowing for rotation. There may be a second bearing 932 for stabilizing the assembly. First bearing 931 and second bearing 932 may be at least one of a ball bearing, a slide bearing, or any other suitable bearing. There may be a housing connector 940 which for example may be fixedly connected to the first housing section 910, for example by a thread and which may be rotatable against the second housing section 920, thus providing a gap thereto. This housing connector 940 may further serve to hold first bearing 931 and/or second bearing 932 in place. The first part may be held by additional studs, screws, clips, or other mounting devices within the first housing section, and the second part may be held by similar parts in the second housing section. The housing has openings for the inspection of the brush and to access power and data connectors for attaching cables.

Thermal pads or thermally conductive glue or paste or thermally conductive compounds may bridge the gap between housing and components, housing and ferrite cores. The cores may be fixed by glue to the PCB.

While FIG. 8 shows a bearing the housing can be used without bearing when both parts are mounted with the housing as mechanical interface within a customer system. Elements mounted to the PCB might serve as parts for the fixation of the housing and connecting the housing with potentials on the PCB, e.g. the brush track.

Figure 9:
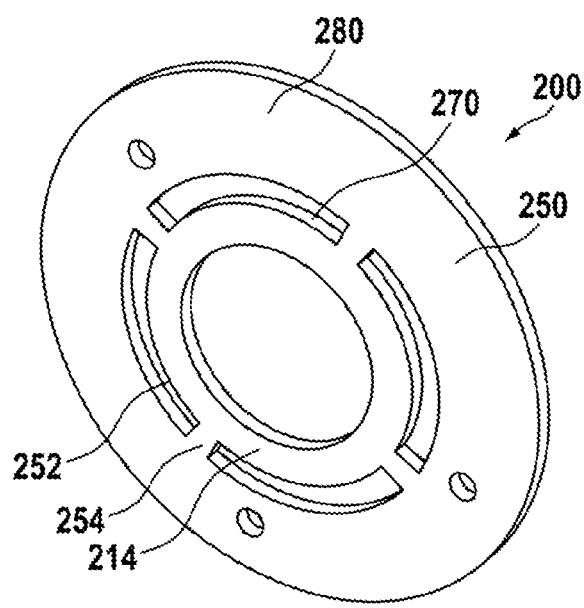
FIG. 9 shows a PCB in a perspective view.

FIG. 9 shows a first PCB 250 in a perspective view. The PCB may have webs 254 and cutouts 252. The magnetic cores 210 may have cutouts, which may be arranged so that they interlock with the webs and cutouts of the PCB. The webs of the PCB may be connecting mechanically and electrically the winding part of the PCB and the part carrying the components of the capacitive link and further electronics required.

Figure 10:
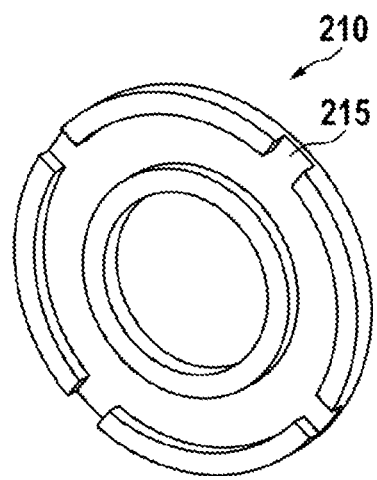
FIG. 10 shows a magnetic core in a perspective view.

FIG. 10 shows a magnetic core in a perspective view. This magnetic core has 4 cutouts 215.

It will be appreciated to those skilled in the art having the benefit of this disclosure that this invention is believed to provide a rotary joint. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 rotary joint
105 plane of rotation
110 rotation axis
120 direction of rotation
200 first part
210 first magnetic core
211 air gap
212 first winding
214 first winding on PCB
215 first magnetic core cutout
250 first PCB
252 first PCB cutout
254 first PCB web
260 sliding brush
261 conductive track
262 flat metal spring brush
263 metal spring
264 contact element
270 first capacitive data link component
280 alternate first capacitive data link component
300 second part
310 second magnetic core
312 second winding
314 second winding on PCB
316 winding termination
350 second PCB
360 sliding track
370 second capacitive data link component
372 second capacitive data link termination
380 alternate second capacitive data link component
382 alternate second capacitive data link termination
391-393 electronic components
800 magnetic stray field
910 first housing section
920 second housing section
931 first bearing
932 second bearing
940 housing connector

The invention claimed is:

1. A disc-type rotary joint comprising a first part and a second part configured to rotate about a rotation axis against the first part,
wherein:
the first part includes at least one first magnetic core, at least one sliding brush, and at least one first capacitive data link component,
the second part includes at least one second magnetic core configured to couple power with the at least one first magnetic core, at least one sliding track configured to galvanically couple with the at least one sliding brush, and at least one second capacitive data link component configured to transfer data from and/or to the at least one first capacitive data link component;
wherein:
the at least one first magnetic core is mounted at a first distance from the at least one second magnetic core thereby forming an airgap between the at least one first magnetic core and the at least one second magnetic core;
wherein:
a first winding is within the at least one first magnetic core and a second winding is within the at least one second magnetic core;
wherein:
the rotary joint is a disc-type rotary joint, and
the at least one sliding track is arranged radially between the at least one second magnetic core and the at least one second capacitive data link component,
wherein:
the first part and the second part are arranged on opposing sides of a common plane that is orthogonal to the rotation axis, and
the at least one sliding track is separated by a second distance from the at least one first capacitive data link component or from the at least one second capacitive data link component, the second distance being larger than a distance between the at least one sliding track and the at least one first magnetic core or than a distance between the at least one sliding track and the at least one second magnetic core.

2. A disc-type rotary joint comprising a first part and a second part configured to rotate about a rotation axis against the first part,
wherein:
the first part includes at least one first magnetic core, at least one sliding brush, and at least one first capacitive data link component,
the second part includes at least one second magnetic core configured to couple power with the at least one first magnetic core, at least one sliding track configured to galvanically couple with the at least one sliding brush, and at least one second capacitive data link component configured to transfer data from and/or to the at least one first capacitive data link component;
wherein:
the at least one first magnetic core is mounted at a first distance from the at least one second magnetic core thereby forming an airgap between the at least one first magnetic core and the at least one second magnetic cores;
wherein:
a first winding is within the at least one first magnetic core and a second winding is within the at least one second magnetic core;
wherein:
the rotary joint is a disc-type rotary joint, and
the at least one sliding track is arranged radially between the at least one second magnetic core and the at least one second capacitive data link component,
wherein:
the first part and the second part are arranged on opposing sides of a common plane that is orthogonal to the rotation axis, and
the first part includes a first printed circuit board (PCB), which further includes an electrically conductive track arranged at the same radial position as the at least one sliding track and which is electrically connected to the at least one sliding brush, wherein an axial distance between the electrically conductive track and the at least one sliding track is smaller than or equal to an extent of the air gap between the at least one first magnetic core and the at least one second magnetic core.

3. A disk-type rotary joint according to claim 2, wherein the at least one conductive track at the first PCB has the same width as that of the at least one sliding track.

4. A disk-type rotary joint according to claim 3, wherein the at least one sliding track is arranged below a plane that is defined by the airgap and wherein the at least one sliding track is mounted above said plane.

5. A disk-type rotary joint according to claim 4,
wherein the first winding in the at least one first magnetic core is at least one PCB trace at the first PCB, and/or
wherein the second part includes a second PCB and the second winding in the at least one second magnetic core is at least one PCB trace at the second PCB.

6. A disk-type rotary joint according to claim 5,
wherein the at least one first magnetic core includes at least one first magnetic core cutout matching with at least one web and with at least one cutout in the first PCB, and/or
wherein the at least one second magnetic core includes at least one second magnetic core cutout matching with at least one web and with at least one cutout in the second PCB.

7. A disk-type rotary joint according to claim 2, wherein the at least one sliding brush is located on an outer side of the first PCB, and the first PCB has a cutout configured to contain a spring in addition to pads that are configured to have the spring mounted by soldering.

8. A disk-type rotary joint according to claim 1, wherein the at least one sliding track has a width that is larger than the first distance between the at least one first magnetic core and the at least one second magnetic core.

9. A disk-type rotary joint according to claim 2, wherein the at least one sliding track has a width that is larger than the first distance between the at least one first magnetic core and the at least one second magnetic core.

10. A disk-type rotary joint according to claim 1, wherein the at least one sliding track has a width larger than at least one of 2 mm, 8 mm, 10 mm, and 15 mm, and smaller than at least one of 50 mm, 40 mm, 30 mm, 20 mm, 10 mm, and 5 mm.

11. A disk-type rotary joint according to claim 2, wherein the at least one sliding track has a width larger than at least one of 2 mm, 8 mm, 10 mm, and 15 mm, and smaller than at least one of 50 mm, 40 mm, 30 mm, 20 mm, 10 mm, and 5 mm.

12. A disk-type rotary joint according to claim 1, wherein the at least one sliding track is separated by a third distance from the at least one first magnetic core or from the at least one second magnetic core, said third distance being smaller than one of 10 times the first distance, 5 times the first distance, 3 times the first distance, and 1 time the first distance.

13. A disk-type rotary joint according to claim 2, wherein the at least one sliding track is separated by a third distance from the at least one first magnetic core or from the at least one second magnetic core, said third distance being smaller than one of 10 times the first distance, 5 times the first distance, 3 times the first distance, and 1 time the first distance.

14. A disk-type rotary joint according to claim 1, wherein the at least one sliding track has at least one galvanized layer configured to reduce contact resistance.

15. A disk-type rotary joint according to claim 2, wherein the at least one sliding track has at least one galvanized layer configured to reduce contact resistance.

16. A disk-type rotary joint according to claim 14, wherein the at least one galvanized layer includes at least one of gold and silver.

17. A disk-type rotary joint according to claim 15, wherein the at least one galvanized layer includes at least one of gold and silver.

18. A disk-type rotary joint according to claim 1, wherein the second part includes a multi-layer PCB and at least one electrically conductive track embedded between at least two insulating layers of the multi-layer PCB, arranged below the at least one electrically conductive track and electrically connected to the at least one sliding track.

19. A disk-type rotary joint according to claim 2, wherein the second part includes a multi-layer PCB and at least one electrically conductive track embedded between at least two insulating layers of the multi-layer PCB, arranged below the at least one electrically conductive track and electrically connected to the at least one sliding track.

20. A disk-type rotary joint according to claim 18, wherein the at least one electrically conductive track embedded between the at least two insulating layers of the multi-layer PCB has multiple electrical contacts to the at least one sliding track.

21. A disk-type rotary joint according to claim 19, wherein the at least one electrically conductive track embedded between the at least two insulating layers of the multi-layer PCB has multiple electrical contacts to the at least one sliding track.

22. A disk-type rotary joint according to claim 20, wherein the at least one sliding brush is located on an outer side of the first PCB, and the first PCB has a cutout configured to contain a spring in addition to pads that are configured to have the spring mounted by soldering.

\* \* \* \* \*